(12) United States Patent
Jain et al.

(10) Patent No.: US 10,973,423 B2
(45) Date of Patent: Apr. 13, 2021

(54) DETERMINING HEALTH MARKERS USING PORTABLE DEVICES

(71) Applicant: Samsung Electronics Co., Ltd., Gyeonggi-Do (KR)

(72) Inventors: Jawahar Jain, Los Altos, CA (US); James Young, Menlo Park, CA (US); Cody Wortham, Mountain View, CA (US); Sajid Sadi, San Jose, CA (US); Pranav Mistry, Campbell, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 366 days.

(21) Appl. No.: 15/957,627

(22) Filed: Apr. 19, 2018

(65) Prior Publication Data

US 2018/0317788 A1 Nov. 8, 2018

Related U.S. Application Data

(60) Provisional application No. 62/501,966, filed on May 5, 2017.

(51) Int. Cl.
*A61B 5/024* (2006.01)
*G16H 40/63* (2018.01)
(Continued)

(52) U.S. Cl.
CPC ...... *A61B 5/02438* (2013.01); *A61B 5/02416* (2013.01); *A61B 5/165* (2013.01);
(Continued)

(58) Field of Classification Search
CPC .... G16H 50/20; G16H 40/63; A61B 5/02438; A61B 5/7253; A61B 5/02416;
(Continued)

(56) References Cited

U.S. PATENT DOCUMENTS

| 9,126,050 B2 | 9/2015 | Simon et al. |
| 9,149,228 B2 | 10/2015 | Kinast |

(Continued)

FOREIGN PATENT DOCUMENTS

| CN | 106175742 A | 12/2016 |
| CN | 110461215 A1 | 11/2019 |

(Continued)

OTHER PUBLICATIONS

WIPO Appln. No. PCTKR2018005202, ISR, dated Aug. 16, 2018, 3 pg.

(Continued)

*Primary Examiner* — Mischita L Henson
(74) *Attorney, Agent, or Firm* — Cuenot, Forsythe & Kim, LLC

(57) ABSTRACT

Processing PPG data using a device can include determining a quality estimate for a segment of PPG data and, in response to determining that the quality estimate exceeds a quality threshold, filtering the segment of the PPG data based upon an estimate of periodicity of the segment of the PPG data. A health marker can be determined for the segment of PPG data. The health marker can be validated based upon a prior determination of the health marker from PPG data. In response to the validation, the health marker can be output.

39 Claims, 3 Drawing Sheets

(51) Int. Cl.
*A61B 5/00* (2006.01)
*A61B 5/16* (2006.01)
*G16H 50/20* (2018.01)
*A61B 5/11* (2006.01)

(52) U.S. Cl.
CPC .......... *A61B 5/7203* (2013.01); *A61B 5/7221* (2013.01); *A61B 5/7253* (2013.01); *G16H 40/63* (2018.01); *G16H 50/20* (2018.01); *A61B 5/02405* (2013.01); *A61B 5/1118* (2013.01); *A61B 5/725* (2013.01); *A61B 2560/0431* (2013.01)

(58) Field of Classification Search
CPC ..... A61B 5/7221; A61B 5/165; A61B 5/7203; A61B 5/1118; A61B 2560/0431; A61B 5/02405; A61B 5/725
See application file for complete search history.

(56) References Cited

U.S. PATENT DOCUMENTS

| | | | |
|---|---|---|---|
| 9,183,351 | B2 | 11/2015 | Shusterman |
| 9,307,917 | B2 | 4/2016 | Hong et al. |
| 9,326,697 | B2 | 5/2016 | Linker |
| 9,339,202 | B2 | 5/2016 | Brockway et al. |
| 9,351,640 | B2 | 5/2016 | Tran |
| 9,375,145 | B2 | 6/2016 | Chin et al. |
| 9,439,599 | B2 | 9/2016 | Thompson et al. |
| 10,231,673 | B2 | 3/2019 | Jain et al. |
| 10,390,764 | B2 | 8/2019 | Jain et al. |
| 10,478,131 | B2 | 11/2019 | Jain et al. |
| 2012/0165691 | A1 | 6/2012 | Ting et al. |
| 2012/0302846 | A1* | 11/2012 | Volmer .................. G06K 9/624 600/324 |
| 2013/0338460 | A1 | 12/2013 | He et al. |
| 2015/0305684 | A1* | 10/2015 | Gross .................. A61B 5/1102 600/301 |
| 2015/0342477 | A1 | 12/2015 | Hingorani et al. |
| 2016/0058367 | A1 | 3/2016 | Raghuram et al. |
| 2016/0128637 | A1 | 5/2016 | Leboeuf et al. |
| 2016/0129310 | A1 | 5/2016 | Ahmed et al. |
| 2016/0278674 | A1 | 9/2016 | Lisogurski |
| 2017/0014037 | A1 | 1/2017 | Coppola et al. |
| 2017/0014040 | A1 | 1/2017 | Shim et al. |
| 2017/0065230 | A1 | 3/2017 | Sinha et al. |
| 2017/0071523 | A1 | 3/2017 | Jain et al. |
| 2017/0071537 | A1 | 3/2017 | Jain et al. |
| 2017/0071551 | A1 | 3/2017 | Jain et al. |
| 2017/0156592 | A1* | 6/2017 | Fu ........................ A61B 5/0452 |

FOREIGN PATENT DOCUMENTS

| | | | |
|---|---|---|---|
| EP | 2861133 A1 | 4/2015 | |
| EP | 3570736 A1 | 11/2019 | |
| KR | 20130059775 | 6/2013 | |
| KR | 20130059775 A * | 6/2013 | .......... A61B 5/0285 |
| KR | 20170008043 | 1/2017 | |
| KR | 20190138733 A | 12/2019 | |
| WO | 2013036718 A1 | 3/2013 | |
| WO | 2015150199 A1 | 10/2015 | |
| WO | 2018203712 A1 | 11/2018 | |

OTHER PUBLICATIONS

WIPO Appln. No. PCTKR2018005202, Written Opinion, dated Aug. 16, 2018, 7 pg.
EP Appln. 18794622.3, Extended European Search Report, dated Jan. 9, 2020, 7 pg.
Parak, J. et al., "Evaluation of the Beat-to-Beat Detection Accuracy of PulseOn Wearable Optical Heart Rate Monitor," In 37th Annual Int'l. Conf. of the IEEE Engineering in Medicine and Biology Society (EMBC), Aug. 25, 2015, pp. 8099-8102.
Zhang, Z., "Photoplethysmography-Based Heart Rate Monitoring in Physical Activities via Joint Sparse Spectrum Reconstruction," IEEE Trans. on Biomedical Engineering, Aug. 2015, vol. 62, No. 8, pp. 1902-1910.
Lai, P.H. et al., "Lightweight wrist photoplethysmography for heavy exercise: motion robust heart rate monitoring algorithm,"In Healthcare Technology Letters, vol. 2, No. 1, pp. 6-11.

* cited by examiner

DETERMINING HEALTH MARKERS USING PORTABLE DEVICES

CROSS-REFERENCE TO RELATED APPLICATIONS

This application claims the benefit of U.S. Provisional Patent Application No. 62/501,966 filed on May 5, 2017, which is fully incorporated herein by reference.

TECHNICAL FIELD

This disclosure relates to determining health markers for users and, more particularly, determining such health markers using portable devices.

BACKGROUND

The popularity of portable devices has increased significantly over the last several years. Examples of portable devices include mobile phones and tablet computers. Another category of portable devices is called "wearable devices." An example of a wearable device is a "smart watch." Many portable devices have a variety of different built in sensors. Some portable devices also have communication ports and/or transceivers allowing the devices to couple to one or more external sensors.

One type of sensor that is routinely included in, or coupled to, a portable device is a photoplethysmogram (PPG) sensor. A PPG sensor is an optical sensor that is capable of generating a volumetric measurement of an organ. For example, a PPG sensor is capable of measuring the modulation of blood flow within a human body in response to the beat-to-beat ejection of blood by the heart into the aorta.

A portable device equipped with a PPG sensor is capable of generating information that may be used to evaluate the health of a user. The data generated by a PPG sensor, however, are very sensitive to noise. Small motions and/or movements in the portable device relative to the user, for example, are often sufficient to introduce significant noise into the data that is generated by the PPG sensor. This noise can render the resulting data virtually unusable.

SUMMARY

In one or more embodiments, a method includes determining a quality estimate for a segment of PPG data and, in response to determining that the quality estimate exceeds a quality threshold, filtering, using a processor, the segment of the PPG data based upon an estimate of periodicity of the segment of the PPG data. The method can include determining, using the processor, a health marker for the segment of the PPG data and validating the health marker based upon a prior determination of the health marker from PPG data. The method can include, in response to the validating, outputting the health marker.

In one or more embodiments, a device includes a memory configured to store instructions and a processor coupled to the memory. The processor, in response to executing the instructions, is configured to initiate operations. The operations can include determining a quality estimate for a segment of PPG data and, in response to determining that the quality estimate exceeds a quality threshold, filtering the segment of the PPG data based upon an estimate of periodicity of the segment of the PPG data. The operations can include determining a health marker for the segment of the PPG data and validating the health marker based upon a prior determination of the health marker from PPG data. The operations can also include, in response to the validating, outputting the health marker.

In one or more embodiments, a computer program product can include a computer readable storage medium having program code stored thereon. The program code is executable by a processor to perform operations. The operations can include determining a quality estimate for a segment of PPG data and, in response to determining that the quality estimate exceeds a quality threshold, filtering the segment of the PPG data based upon an estimate of periodicity of the segment of the PPG data. The operations can include determining a health marker for the segment of the PPG data and validating the health marker based upon a prior determination of the health marker from PPG data. The operations can also include, in response to the validating, outputting the health marker.

This Summary section is provided merely to introduce certain concepts and not to identify any key or essential features of the claimed subject matter. Many other features and embodiments of the invention will be apparent from the accompanying drawings and from the following detailed description.

BRIEF DESCRIPTION OF THE DRAWINGS

The accompanying drawings show one or more embodiments; however, the accompanying drawings should not be taken to limit the invention to only the embodiments shown. Various aspects and advantages will become apparent upon review of the following detailed description and upon reference to the drawings.

DETAILED DESCRIPTION

Figure 1:
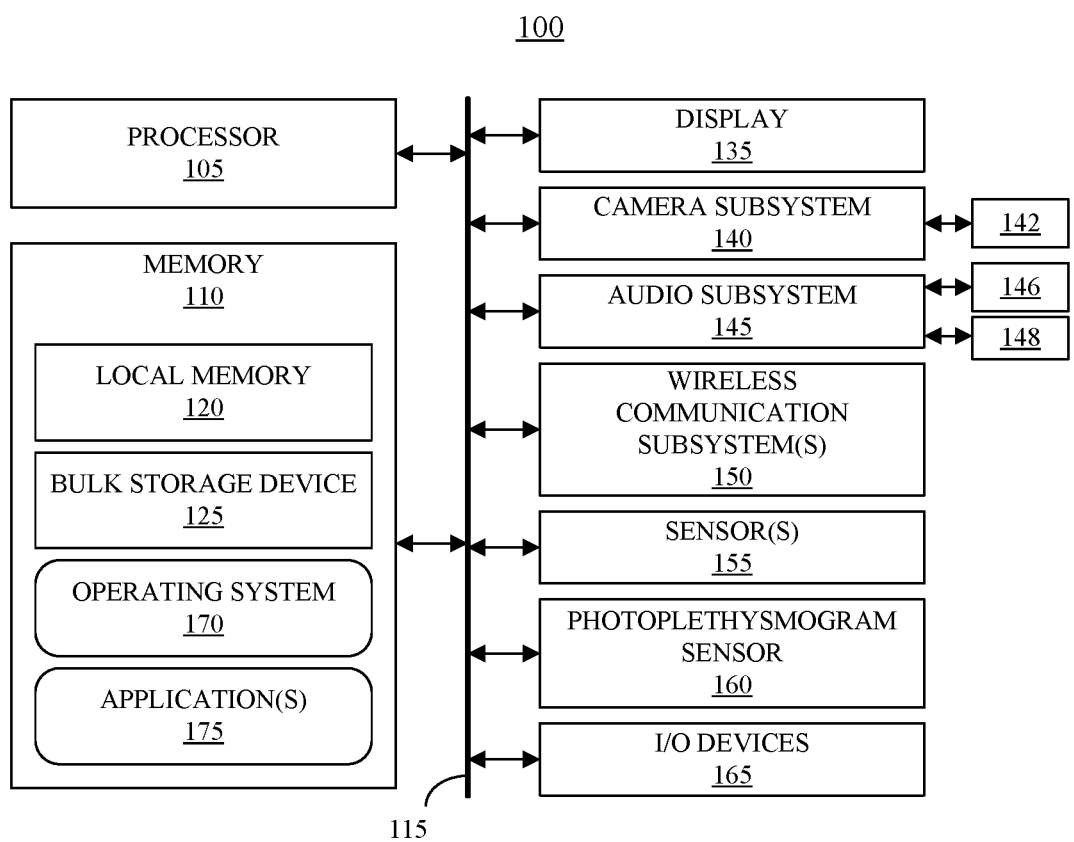
FIG. 1 illustrates an example architecture for a device.

While the disclosure concludes with claims defining novel features, it is believed that the various features described herein will be better understood from a consideration of the description in conjunction with the drawings. The process (es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to determining health markers for users and, more particularly, determining such health markers for users requires accurate measurement and analysis of photoplethysmogram (PPG) data. As defined within this disclosure, the term "PPG data" means data that is generated by a PPG sensor that is within (e.g., part of) a portable device or coupled to a portable device. Examples of health markers that may be determined from PPG data can include, but are not limited to, heart rate, heart rate variability (HRV), stress, blood pressure, respiration, and arterial tone. Accurate assessment of health markers from PPG data allows portable devices to be used in reliably managing different medical conditions. For example, portable devices may be used in managing diabetes, hypertension, cardiovascular diseases, pulmonary diseases, mood disorder, and substance-abuse. Further, accurate assessment of health markers also allows portable devices to assess quality of life of individuals with greater accuracy.

The high sensitivity of PPG sensors to noise often results in wide variability in the PPG data that is generated. In the case of wearable devices equipped with PPG sensors, for example, the PPG data that is generated is highly sensitive to artifacts induced by motion of the portable device relative to the individual wearing the wearable device. Even small amounts of motion can produce wide variation in the resulting PPG data, thereby significantly limiting the usefulness of the portable devices for purposes of monitoring user health.

In accordance with the inventive arrangements described within this disclosure, a portable device equipped with a PPG sensor is capable of generating PPG data. The portable device is capable of distinguishing between different segments of PPG data based upon a quality assessment. The portable device is capable of identifying those segments of PPG data of lesser quality that are more likely to result in an incorrect prediction or estimate of one or more health markers. In particular embodiments, the portable device is capable of discarding segments of PPG data determined to be of lesser quality so that such segments are not used to predict health marker(s) for the user. The portable device is also capable of generating notifications indicating the insufficiency of PPG data. The notifications, for example, may indicate that adjustment of the portable device may be necessary to obtain higher quality PPG data, which facilitates greater accuracy in the health markers that are determined.

In one or more embodiments, a portable device is capable of applying multidimensional analysis to the PPG data. Each dimension of the multidimensional analysis is capable of evaluating a different aspect of the PPG data not evaluated by any other dimension of the multidimensional analysis. The portable device may determine that particular segments of PPG data are of insufficient quality based upon one of the dimensions or any combination of two or more of the dimensions of the multidimensional analysis that is performed. Discarding segments of PPG data of low quality allows the portable device to avoid generating inaccurate and/or misleading health markers.

In one or more embodiments, the portable device is capable of analyzing the PPG data in near real time. In performing near real time processing of the PPG data, the portable device is capable of comparing current or more recently determined health marker(s) with prior determined (e.g., historical) health marker(s) to validate the accuracy of the currently determined health markers. Near real time processing, as described herein, facilitates increased accuracy over other techniques that attempt to perform real time prediction of health markers. In particular embodiments, the portable device is capable of performing further validation of the health markers in a post hoc manner. The validation that is performed may include correction of certain segments of the PPG data.

Further aspects of the inventive arrangements are described below in greater detail with reference to the figures. For purposes of simplicity and clarity of illustration, elements shown in the figures are not necessarily drawn to scale. For example, the dimensions of some of the elements may be exaggerated relative to other elements for clarity. Further, where considered appropriate, reference numbers are repeated among the figures to indicate corresponding, analogous, or like features.

FIG. 1 illustrates an example architecture 100 for a device for use with one or more embodiments described within this disclosure. Architecture 100 may be used to implement a data processing system, a communication device, or other system that is suitable for storing and/or executing program code. In particular embodiments, architecture 100 may be used to implement a portable device. For example, architecture 100 may be used to implement a mobile phone, a tablet computer, a portable computer (e.g., a laptop computer), a wearable device such as a smart watch or other fitness device worn by a user.

In the example of FIG. 1, architecture 100 includes at least one processor 105. Processor 105 is coupled to memory 110 through interface circuitry 115. Architecture 100 stores computer readable instructions (also referred to as "program code") within memory 110. Memory 110 is an example of computer readable storage media. Processor 105 executes the program code accessed from memory 110 via interface circuitry 115.

Memory 110 includes one or more physical memory devices such as, for example, a local memory 120 and a bulk storage device 125. Local memory 120 is implemented as one or more non-persistent memory devices used during actual execution of the program code. Examples of local memory 120 include random-access memory (RAM) and/or any of the various types of RAM (e.g., static RAM, dynamic RAM) that are suitable for use by a processor during execution of program code. Bulk storage device 125 is implemented as one or more persistent data storage devices. Examples of bulk storage device 125 include a hard disk drive (HDD), a solid-state drive (SSD), flash memory, a read-only memory (ROM), an erasable programmable read-only memory (EPROM), electrically erasable programmable read-only memory (EEPROM), or other suitable memory. Architecture 100 may also include one or more cache memories (not shown) that provide temporary storage of at least some program code in order to reduce the number of times program code must be retrieved from a bulk storage device during execution.

Examples of interface circuitry 115 include, but are not limited to, an input/output (I/O) subsystem, an I/O interface, a bus system, and a memory interface. For example, interface circuitry 115 may be implemented as any of a variety of bus structures and/or combinations of bus structures including a memory bus or memory controller, a peripheral bus, an accelerated graphics port, and a processor or local bus.

In one or more embodiments, processor 105, memory 110, and/or interface circuitry 115 are implemented as separate components. In one or more embodiments, processor 105, memory 110, and/or interface circuitry 115 are integrated in one or more integrated circuits. The various components in architecture 100, for example, can be coupled by one or more communication buses or signal lines (e.g., interconnects and/or wires). In particular embodiments, memory 110 is coupled to interface circuitry 115 via a memory interface, e.g., a memory controller (not shown).

Architecture 100 may include a display 135. In particular embodiments, display 135 is implemented as touch-sensitive or touchscreen display capable of receiving touch input from a user. A touch sensitive display and/or a touch-sensitive pad is capable of detecting contact, movement, gestures, and breaks in contact using any of a variety of available touch sensitivity technologies. Example touch sensitive technologies include, but are not limited to, capacitive, resistive, infrared, and surface acoustic wave technologies, and other proximity sensor arrays or other elements for determining one or more points of contact with a touch sensitive display and/or device.

Architecture 100 may include a camera subsystem 140. Camera subsystem 140 can be coupled to interface circuitry 115 directly or through a suitable input/output (I/O) controller. Camera subsystem 140 can be coupled to an optical sensor 142. Optical sensor 142 may be implemented using any of a variety of technologies. Examples of optical sensor 142 can include, but are not limited to, a charged coupled device (CCD) or a complementary metal-oxide semiconductor (CMOS) optical sensor. Camera subsystem 140 and optical sensor 142 are capable of performing camera functions such as recording images and/or recording video.

Architecture 100 may include an audio subsystem 145. Audio subsystem 145 can be coupled to interface circuitry 115 directly or through a suitable input/output (I/O) controller. Audio subsystem 145 can be coupled to a speaker 146 and a microphone 148 to facilitate voice-enabled functions, such as voice recognition, voice replication, digital recording, and telephony functions.

Architecture 100 may include one or more wireless communication subsystems 150. Each of wireless communication subsystem(s) 150 can be coupled to interface circuitry 115 directly or through a suitable I/O controller (not shown). Each of wireless communication subsystem(s) 150 is capable of facilitating communication functions. Examples of wireless communication subsystems 150 can include, but are not limited to, radio frequency receivers and transmitters, and optical (e.g., infrared) receivers and transmitters. The specific design and implementation of wireless communication subsystem 150 can depend on the particular type of architecture 100 implemented and/or the communication network(s) over which architecture 100 is intended to operate.

As illustrative and non-limiting examples, wireless communication subsystem(s) 150 may be designed to operate over one or more mobile networks (e.g., GSM, GPRS, EDGE), a WiFi network which may include a WiMax network, a short-range wireless network (e.g., a Bluetooth® network), NFC, and/or any combination of the foregoing. Wireless communication subsystem(s) 150 can implement hosting protocols such that architecture 100 can be configured as a base station for other wireless devices.

Architecture 100 may include one or more sensors 155. Each of sensors 155 can be coupled to interface circuitry 115 directly or through a suitable I/O controller (not shown). Examples of sensors 155 that can be included in architecture 100 include, but are not limited to, a motion sensor, a light sensor, and a proximity sensor to facilitate orientation, lighting, and proximity functions, respectively, of a device using architecture 100. Other examples of sensors 155 can include, but are not limited to, a location sensor (e.g., a GPS receiver and/or processor) capable of providing geo-positioning sensor data, an electronic magnetometer (e.g., an integrated circuit chip) capable of providing sensor data that can be used to determine the direction of magnetic North for purposes of directional navigation, an accelerometer capable of providing data indicating change of speed and direction of movement of a device using architecture 100 in 3-dimensions, and an altimeter (e.g., an integrated circuit) capable of providing data indicating altitude.

Architecture 100 may include a PPG sensor 160. PPG sensor 160 can be coupled to interface circuitry 115 directly or through a suitable I/O controller (not shown). PPG sensor 160 may be implemented as an optical sensor. PPG sensor 160 is capable of generating a PPG, e.g., PPG data, for a user. A PPG is an optically obtained plethysmogram. In general, a PPG is a volumetric measurement of an organ. In one or more embodiments, PPG sensor 160 is implemented as a pulse oximeter which illuminates the skin and measures changes in light absorption to determine amount of oxygen carried in the blood. In particular embodiments, PPG sensor 160 is a multichannel PPG sensor (e.g., having light-emitting diodes capable of generating light of different wavelengths). PPG sensor 160 may be used to determine one or more health markers and/or to determine one or more surrogate markers of one or more health markers. In one or more embodiments, health markers are also referred to as "vital signs".

Within this disclosure, the term "PPG data" is used to refer to the data that is generated by and output from a PPG sensor as previously described. Within this disclosure, the terms "PPG data" and "PPG signal" may be used interchangeably from time-to-time. It should be appreciated that PPG signal(s) are specified directly by PPG data.

Architecture 100 further may include one or more input/output (I/O) devices 165 coupled to interface circuitry 115. I/O devices 165 may be coupled to architecture 100, e.g., interface circuitry 115, either directly or through intervening I/O controllers (not shown). Examples of I/O devices 165 include, but are not limited to, a track pad, a keyboard, a display device, a pointing device, one or more communication ports (e.g., Universal Serial Bus (USB) ports), a network adapter, and buttons or other physical controls. A network adapter refers to circuitry that enables architecture 100 to become coupled to other systems, computer systems, remote printers, and/or remote storage devices through intervening private or public networks. Modems, cable modems, Ethernet interfaces, and wireless transceivers not part of wireless communication subsystem(s) 150 are examples of different types of network adapters that may be used with architecture 100. One or more of I/O devices 165 may be adapted to control functions of one or more or all of sensors 155 and/or one or more of wireless communication subsystem(s) 150.

Memory 110 stores program code. Examples of program code include, but are not limited to, routines, programs, objects, components, logic, and other data structures. For purposes of illustration, memory 110 stores an operating system 170 and application(s) 175. Applications 175 can include, for example, a PPG signal processing application. In one or more embodiments, the PPG signal processing application, when executed, is capable of causing a device implemented using architecture 100 and/or other devices that may be communicatively linked with the device implemented using architecture 100, to perform the various operations described herein. Memory 110 is also capable of storing data, whether data utilized by operating system 170, data utilized by application(s) 175, data received from user inputs, data generated by one or more or all of sensor(s) 155 and/or PPG sensor 160, data received and/or generated by camera subsystem 140, data received and/or generated by audio subsystem 145, and/or data received by I/O devices 165.

In an aspect, operating system 170 and application(s) 175, being implemented in the form of executable program code, are executed by architecture 100 and, more particularly, by processor 105, to perform the operations described within this disclosure. As such, operating system 170 and application(s) 175 may be considered an integrated part of architecture 100. Further, it should be appreciated that any data and/or program code used, generated, and/or operated upon by architecture 100 (e.g., processor 105) are functional data structures that impart functionality when employed as part of architecture 100.

Memory 110 is also capable of storing additional program code. Examples of additional program code include, but are not limited to, instructions that facilitate communicating with one or more additional devices, one or more computers and/or one or more servers; graphic user interface (GUI) and/or UI processing; sensor-related processing and functions; phone-related processes and functions; electronic-messaging related processes and functions; Web browsing-related processes and functions; media processing-related processes and functions; GPS and navigation-related processes and functions; security functions; and camera-related processes and functions including Web camera and/or Web video functions.

Architecture 100 further can include a power source (not shown). The power source is capable of providing electrical power to the various elements of architecture 100. In an embodiment, the power source is implemented as one or more batteries. The batteries may be implemented using any of a variety of known battery technologies whether disposable (e.g., replaceable) or rechargeable. In another embodiment, the power source is configured to obtain electrical power from an external source and provide electrical power (e.g., direct current (DC) power) to the elements of device. In the case of a rechargeable battery, the power source further may include circuitry that is capable of charging the battery or batteries when coupled to an external power source.

Architecture 100 is provided for purposes of illustration and not limitation. A device and/or system configured to perform the operations described herein may utilize an architecture that differs from architecture 100 of FIG. 1. Such other architecture may be a simplified version of architecture 100 that includes a memory capable of storing instructions and a processor capable of executing instructions. In this regard, architecture 100 may include fewer components than shown or additional components not illustrated in FIG. 1 depending upon the particular type of device that is implemented. In addition, the particular operating system and/or application(s) included may vary according to device type as may the types of I/O devices 165 included. Further, one or more of the illustrative components may be incorporated into, or otherwise form a portion of, another component. For example, a processor may include at least some memory.

In one or more embodiments, a device implemented using an architecture the same as or similar to the architecture of FIG. 1 is capable of performing a near real time processing of PPG data. In particular embodiments, the device is capable of implementing a cascaded processing technique where each different processing stage is capable of generating a more refined representation of the PPG data. Each stage, for example, may represent one or more dimensions of the multidimensional analysis that is performed and is capable of passing the generated representation(s) on to the next stage in the cascade. Portions of the computations performed in the prior stages may be used in the subsequent stage or stages. In particular embodiments, the cascaded approach utilizes orthogonal processing techniques within the various stages. The orthogonality of the techniques refers to each stage operating on a different and/or independent aspect of the PPG data.

In one or more embodiments, the near real time analysis performed by the device facilitates evaluation of particular health markers such as heart rate relative to a baseline of the health marker. For example, particular health markers are Autonomic Nervous System (ANS) measurements that may only be evaluated relative to a baseline. As an illustrative and non-limiting example, near real time analysis allows the device to compare a health marker such as heart rate of the user to the user's heart rate from some time in the recent past. For example, the device may compare a current heart rate determination with one determined several seconds ago (e.g., 10, 20, 30, 40, 50, or 60 seconds before). Through this comparison, the device is capable of determining how the health marker has changed for the user and/or validating the health marker(s).

Figure 2:
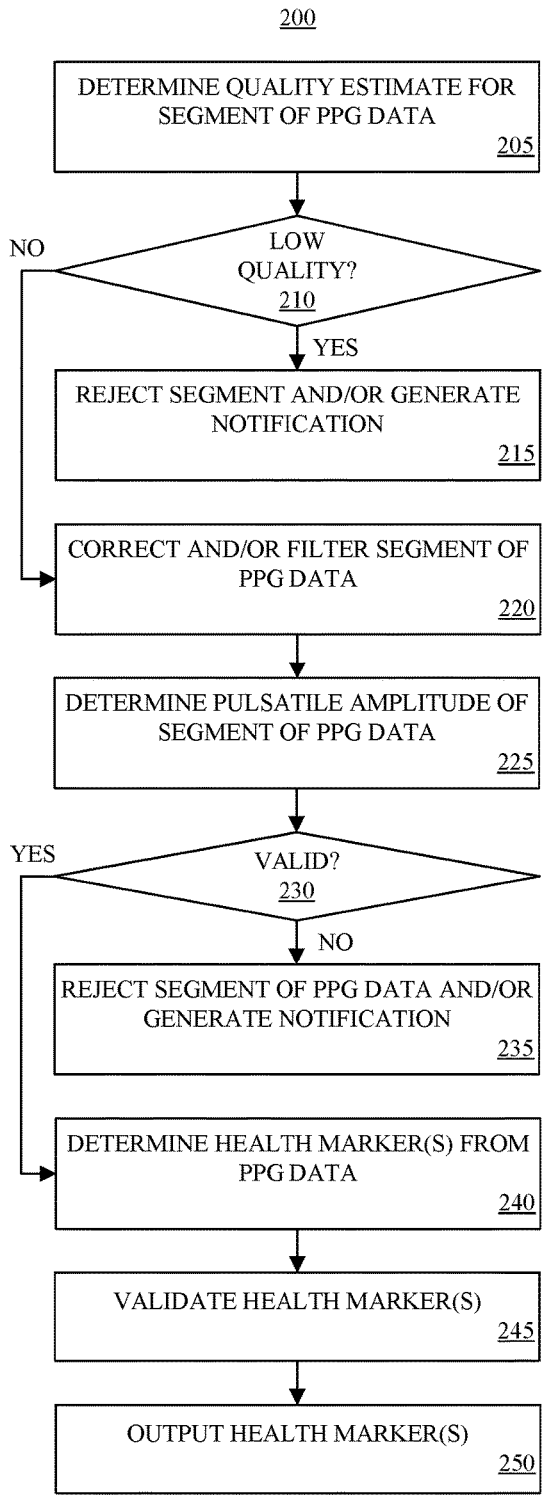
FIG. 2 illustrates an example method of processing photoplethysmogram (PPG) data.

FIG. 2 illustrates an example method 200 of processing PPG data. Method 200 may be performed by a portable device having an architecture the same as or similar to the architecture described in connection with FIG. 1. Method 200 may be implemented as a near real time processing technique. In one or more embodiments, method 200 may be performed on a per-segment basis. A segment refers to a defined window of time for PPG data. The window may be defined as PPG data within a given span of time. The span of time may one or more seconds (e.g., 5, 10, 20, 30, 40, 50, or 60 seconds). In another example, the window may be defined as a predetermined number of PPG data samples. In particular embodiments, the segment of PPG data may be a sliding window that is moved across the PPG data.

Method 200 may begin in a state where the device is receiving PPG data from a PPG sensor. In general, method 200 describes processing of a particular segment of PPG data. It should be appreciated that method 200 may be repeated to continue processing further segments of PPG data as the window is moved across the PPG data in time.

In block 205, the device determines a quality estimate for a segment of the PPG data. In one or more embodiments, the device is capable of determining a signal-to-noise ratio (SNR) for the PPG data. The SNR may be determined on a per segment basis. The SNR measurement allows the device to identify segments of PPG data where there is a paucity of the PPG signal. Further aspects of block 205 are described herein in greater detail in connection with FIG. 3.

In block 210, the device determines whether the segment of PPG data is of low quality. For example, the device is capable of comparing the quality estimate of the segment of PPG data from block 205 with a quality threshold. The quality threshold may be a predetermined SNR below which the PPG data is deemed to be of little or no value. For example, for segments of PPG data with a quality estimate that does not exceed the quality threshold, any health markers determined or estimated using such data are unreliable. In response to determining that the segment of PPG data is of low quality (e.g., the quality estimate does not exceed the quality threshold), method 200 continues to block 215. In response to determining that the segment of PPG data is not of low quality (e.g., the quality estimate exceeds the quality threshold), method 200 continues to block 220.

In block 215 the device rejects the segment of PPG data. For example, the device is capable of deleting the segment having a quality level that does not exceed the quality threshold. In particular embodiments, in rejecting the segment, the device does not attempt to determine any health markers using the segment of PPG data. Further, the device is capable of providing a notification indicating that the segment of PPG data is not suitable for use in determining health markers. In one or more embodiments, the notification may provide instructions to the user to adjust the device to obtain higher quality PPG data in the future. As noted, though not illustrated in FIG. 2, method 200 may begin anew to process further segments of PPG data.

In block 220, the device corrects and/or filters the segment of PPG data. In one or more embodiments, the device is capable of performing a correction process on the segment that includes de-noising the segment of PPG data. The device is also capable of performing filtering on the segment of the PPG data. In particular embodiments, the device performs a dynamic filtering process where the particular filter that is applied is selected from a plurality of different available filters based upon one or more attributes of the segment of PPG data itself. Further aspects of block 220 are described herein in greater detail in connection with FIG. 4. In one or more embodiments, the device selects the particular filter that is applied based upon periodicity of the segment of PPG data.

In block 225, the device optionally determines the pulsatile amplitude of the segment of PPG data. The device is capable of performing a running estimate of variance or covariance in the PPG data to distinguish between PPG data collected from organic objects that have detectable heartbeats and organic objects that do not have detectable heartbeats. In the case where the PPG sensor is a single wavelength sensor (e.g., is not multi-channel), the PPG signal variance increases with the dynamics of the blood flow. This increase in signal variance leads to a pulse pressure wave that alternates between maximum and minimum amplitudes. In the presence of a heartbeat, the pulsatile amplitude represents pulsation of arterial blood.

The DC level of the PPG signal (e.g., the mean value of a periodic function) represents the non-pulsatile component of the blood. The non-pulsatile component of the blood includes non-pulsatile arterial blood, venous blood, and absorption from background tissues (e.g., bones, cartilage, and extra-cellular fluids). In the human body, the pulsatile component is typically at most 10% of the total PPG signal. This property is not obeyed in PPG signals where the source of PPG signal being sensed by the PPG sensor is just a reflection from an inert surface. In cases where the PPG signal is a reflection from an inert surface, the pulsatile amplitude can vary erratically with respect to the DC level of the signal. For example, when the ratio of the AC component and the DC component of PPG signal is larger than 0.1 or smaller than 0.01, the device is capable of determining that the PPG signal that is obtained is not modulated by blood.

In embodiments where the PPG sensor is multichannel, the device is capable of determining covariance in the PPG data between the PPG signal generated using a first channel of the PPG sensor and the PPG signal generated using the second channel of the PPG sensor. The device is capable of determining that the PPG data does represent a blood flow when above a predetermined threshold.

In block 230, the device determines whether the segment of PPG data is valid. For example, in the case where the device measures pulsatile amplitude, the device is capable of determining whether the pulsatile amplitude is within a defined range corresponding to a valid PPG signal. A valid PPG signal is a PPG signal where the pulsatile amplitude is between approximately 0.01 and 0.1 (for a single channel PPG sensor). For example, the device determines whether $0.01 \leq$ pulsatile amplitude $\leq 0.1$ is true. In the case of a multichannel PPG sensor, the device is capable of determining whether the covariance exceeds a threshold. In response to determining that the segment is valid (e.g., where $0.01 \leq$ pulsatile amplitude $\leq 0.1$ is true for a single channel PPG sensor or where the covariance exceeds a threshold for a multichannel PPG sensor), method 200 continues to block 240. In response to determining that the segment is not valid, method 200 continues to block 235.

In block 235, the device is capable of rejecting the segment of PPG data and/or generating a notification. For the device is capable of rejecting the segment as previously described. In rejecting the segment, for example, the device does not attempt to determine any health markers using the segment of PPG data. Further, the device is capable of providing a notification indicating that the segment of PPG data is not suitable for use in determining health markers. In one or more embodiments, the notification may provide instructions to the user to adjust the device to obtain higher quality PPG data in the future.

In block 240, the device is capable of determining one or more health markers from the PPG data. Examples of the different varieties of health markers that the device is capable of determining from the PPG data include, but are not limited to, heart rate, heart rate variability (HRV), stress, blood pressure, respiration, and arterial tone. For example, the device is capable of determining the PPG RR interval (where "RR" is the interval between successive Rs and R represents a peak of the PPG). The PPG RR interval is HRV for the user. As known, HRV is the physiological phenomenon of variation in the time interval between heart beats. HRV is measured by the variation in the beat-to-beat interval. The device is capable of determining the inverse of HRV and scaling the result to obtain an estimate of heart rate. The device is further capable of determining stress for the user. The device is capable of determining stress by taking the derivative of the HRV.

The device is capable of determining blood pressure for the user based upon the area under the curve (AUC) of the PPG signal. The device, for example, is capable of determining systolic blood pressure for the user based upon the AUC of a PPG signal. Larger AUC corresponds to higher systolic blood pressure. As an illustrative and non-limiting example, some studies have found that very low frequency (VLF) fluctuations of systolic blood pressure are related to PPG where systolic blood pressure was found to have a correlation coefficient of approximately −0.81 with VLF fluctuations of PPG amplitude (AM) and a correlation coefficient of approximately 0.83 with PPG baseline (BL) over 10-minute time periods.

In block 245, the device is capable of validating the health marker(s) determined in block 240. In one or more embodiments, the device validates the health marker based upon prior determinations of the health marker for the user. In an example, the device is capable of determining whether the health marker determined in block 240 is within a predetermined physiological range for the health marker in human beings. A measure of heart rate can be compared with a known range of heart rate. An HRV can be compared with a known range of HRV. As described in greater detail herein, the physiological range to which the health metric is compared may be adjusted based upon inertial sensor data.

In another example, the device is capable of validating the health marker by determining whether the health marker determined in block 240 is within a predetermined amount of the same type of health marker measured immediately prior in a time series of such health markers. The device, for example, is capable of determining whether the amount of change observed in the health marker in a time series of such health markers is within acceptable levels.

In one or more embodiments, the validation performed in block 245 includes performing post hoc correction on the segment of PPG data. The device is capable of applying one or more corrective techniques to the segment of PPG data in some cases. Further aspects relating to validation are described in greater detail in connection with FIG. 5.

In block 250, the device is capable of outputting the health marker(s) determined in block 240. More particularly, the device is capable of outputting the health marker(s) determined in block 240 in response to successfully validating each such health marker.

Figure 3:
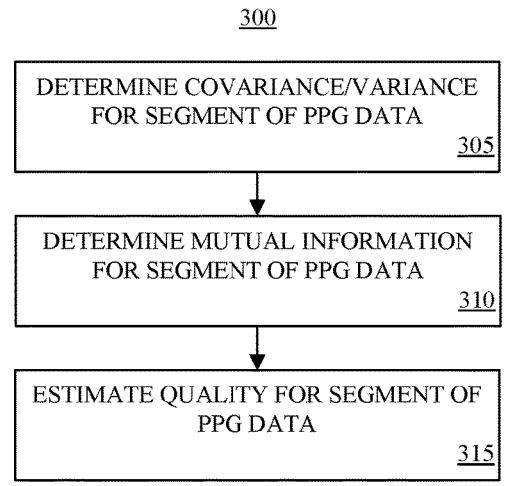
FIG. 3 illustrates an example method of quality estimation for PPG data.

FIG. 3 illustrates an example method 300 of quality estimation for the PPG data. Method 300 may be performed by a device as described herein in connection with FIG. 1. In one or more embodiments, method 300 may be performed by the device to implement block 205 of FIG. 2.

In block 305, the device optionally determines covariance for the segment of PPG data. In one or more embodiments, where the PPG sensor is a multichannel PPG sensor, the device is capable of determining covariance of the PPG signal from a channel of the PPG sensor (e.g., first LED having a first wavelength such as red) to the PPG signal from a second channel of the PPG sensor (e.g., a second LED having a second wavelength such as infrared). In particular embodiments, the device optionally determines variance as described in connection with block 205 of FIG. 2.

In block 310, the device determines mutual information for the segment of PPG data. Mutual information is a quantity that indicates the average amount of data (e.g., bits of data) a given measurement x(t) provides for another measurement x(t+T) taken at a later time. More formally, mutual information is defined as the average amount of information (e.g., in bits) that one random variable provides about another random variable. Expression 1 below illustrates mutual information (MI) expressed as an equation.

$$MI(\tau) = \sum_{x(i), x(i+\tau)} P(x(i), x(i+\tau)) \log_2 \frac{P(x(i), x(i+\tau))}{P(x(i))P(x(i+\tau))} \quad (1)$$

Expression 1 indicates a high degree of mutual information for a delay corresponding to a periodic signal. The mutual information will be relatively high for a periodic signal given a small delay ($\tau$) since the two data sets being compared do not differ by much. As $\tau$ gets larger there is less information the non-delayed measurement x(t) provides about x(t+$\tau$). The drop in mutual information continues until the delay corresponds to the periodicity of the signal (if periodicity in the signal is present).

In block 310, as part of determining mutual information for the PPG data, the device is capable of determining a variety of different quantities. In one or more embodiments, the device determines a measure of SNR. The device, for example, determines peak SNR. The device may also determine the width in reference to the characteristic width of the peak seen in the information spectrum. As an example, the width may be the full-width half-max (FWHM) of a particular peak. In general, the presence of white noise causes the FWHM to be lower as there are more points in the regions surrounding the peak. Since block 310 is part of a normalized, windowed-approach, the peak maximum is lower with respect to adjacent lags. The device may also determine an estimate of the period of the PPG signals specified by the PPG data.

In block 315, the device is capable of estimating quality for the segment of PPG data (e.g., signal quality). In one or more embodiments, the device may classifies the signal quality as low, moderate, or high. For example, the device is capable of comparing a quality score to predetermined ranges for the quality score that are mapped to the different classifications of signal quality. The device is capable of assigning a signal quality to the segment of PPG data based upon which range the quality score falls.

In one or more embodiments, the quality score may be the measure of SNR. In one or more other embodiments, quality score may be determined using the covariance and/or variance and the measure of SNR. As an illustrative and non-limiting example, the device is capable of calculating the quality score by multiplying the covariance and/or variance by a weighting factor and multiplying the measure of SNR by another weighting factor and summing the results. In any case, the device estimates the quality of the segment of PPG data as being low, moderate, or high and outputs the estimated quality. As described in connection with FIG. 2, block 210 is capable of evaluating the signal quality to either continue processing the segment of PPG data or reject the segment of PPG data based upon the estimated quality.

The following discussion illustrates an example method for determining mutual information in a segment of PPG data as performed by the device and as described herein connection with block 310 of FIG. 3. The device is capable of saving the segment of PPG data. As discussed, the segment of PPG data, also referred to as a data array x, is for a particular window. The PPG data may be detrended and filtered PPG samples. In an example, the segment of PPG data may include 200 samples. The number of samples may be within a range where the lower end of the range is small enough to be within a respiratory sinus arrhythmia (RSA) cycle to avoid gradual periodicity drift and where the upper end of the range is large enough to include a $\Delta t = \tau$ that is small enough to enable detection of specific frequency components of interest (e.g., heart rate). Other sample sizes may be used. The example provided herein is for purposes of illustration and not limitation.

The device is capable of generating delayed points from the PPG data. In one or more embodiments, the device is capable of generating a data array, from data array x, that is delayed by $\tau$, where $\tau$ is changed from 1 to N thereby producing N different (delayed) data arrays. Once the data arrays are generated, the device is capable of calculating the mutual information between X and X(t+$\tau$). The device is capable of storing the mutual information in another data array in order of increasing $\tau$.

To calculate the average mutual information, the device processes the array of time-series values X with length N. The device is capable of normalizing X and vertically shifting the data to begin at zero. For example, the device is capable of subtracting the minimum value and then dividing by the maximum value as illustrated in Expressions 2 and 3 below.

$$x_i^* = \sum x_i - x_{min} \quad (2)$$

$$\hat{x}_i = \frac{x_i^*}{x_{max}^*} \quad (3)$$

The device is capable of delaying the data in $\hat{X}$ by $\tau$ resulting in $\hat{Y}$. $\hat{Y}$ is a delayed-image of $\hat{X}$. The device is capable of calculating the mutual information using V.

In one or more embodiments, the device is capable of breaking the distribution functions into a predetermined number of bins. Since this is a 2-dimensional portrait of $\hat{X}\hat{Y}$ in this example, the partitions may be 2-d box partitions. In particular embodiments, the bin size may be constant and may be calculated using Expression 4 below.

$$n = [1 + \log_2(N-\tau) + \tfrac{1}{2}] \tag{4}$$

Based upon Expression 4, there are $N^2$ boxes in this phase portrait. In the example of Expression 4, N is the length of $\hat{X}$ and $\hat{Y}$. In cases where the bins are too large, the distribution has more points per bin and increases in accuracy. The processor of the device may not be capable of tracking changes in mutual information over short distances (time lags) since the bins are too large. In cases where the bin size is smaller, the accuracy drops, but the overall resolution is increased.

In one or more other embodiments, the number of bins may be dynamically adapted during operation. The device is capable of adapting the number of bins so that the number of bins is non-constant for regions of phase space.

In particular embodiments, at this point, the device is capable of checking variance. In practice, the variance will not be zero. If, however, the variance is calculated as zero, the mutual information would also be zero.

The device uses box-search variables $s_1$ and $s_2$, where a specific box corresponds to a point $(s_{1i}, s_{2j})$. The device is capable of traversing the box-search variables for every instance of T. In particular embodiments, the device is capable of performing the traversal using a nested for-loop in implementation. For example, $s_2$ may be a partition along the inner-horizontal axis of phase space, while $s_1$ is a partition along the inner-vertical axis of phase space. With reference to Expressions 5-14 below, p refers to the joint probability distribution, $p_x$ refers to the probability distribution of $\hat{X}$, and $p_y$ refers to the probability distribution of V. The device is capable of finding all instances of $\hat{X}$ that satisfy the conditions defined by Expressions 5-14.

$$C_1: \frac{s_{1i}-1)}{n} < \hat{x}_k; \text{ with } \{k=1,2,\ldots n-\tau\} \tag{5}$$

$$C_2: \frac{s_{1i}}{n} \geq \hat{x}_k; \text{ with } \{k=1,2,\ldots n-\tau\} \tag{6}$$

$$C_3: \frac{(s_{2j}-1)}{n} < \hat{x}_k; \text{ with } \{k=1+\tau, 2+\tau, \ldots n\} \tag{7}$$

$$C_4: \frac{s_{2j}}{n} \geq \hat{x}_k; \text{ with } \{k=1+\tau, 2+\tau, \ldots n\} \tag{8}$$

$$C_{s_{1i},s_{2j}} = 1 \text{ if all } C_p \text{ are true} \tag{9}$$

$$G_{s_{1i},s_{2j}} = 1 \text{ if both } C_1 \text{ and } C_2 \text{ are true} \tag{10}$$

$$F_{s_{1i},s_{2j}} = 1 \text{ if both } C_3 \text{ and } C_4 \text{ are true} \tag{11}$$

$$p = \frac{\sum_{s_{1i}=1}^{n} \sum_{s_{2j}=1}^{n} C_{s_{1i},s_{2j}}}{N-\tau} \tag{12}$$

$$p_x = \frac{\sum_{s_{1i}=1}^{n} \sum_{s_{2j}=1}^{n} G_{s_{1i},s_{2j}}}{N-\tau} \tag{13}$$

$$p_y = \frac{\sum_{s_{1i}=1}^{n} \sum_{s_{2j}=1}^{n} F_{s_{1i},s_{2j}}}{N-\tau} \tag{14}$$

In this example, the technique described loses data since the process requires pairs of values. By time delaying the data, the end points are eliminated with increasing $\tau$. As such, the N−$\tau$ argument is used in the normalizing denominator above in Expressions 12-14.

The device is capable of determining a final mutual information given the probabilities p, $p_x$, and $p_y$ using Expression 15 below, which is the same as Expression 1.

$$MI(\tau) = p * \log_2 \frac{p}{p_x p_y} \tag{15}$$

The foregoing calculations may be repeated for every value of $\tau$ to obtain a distribution of mutual information over all delays. The device is further capable of performing peak detection on the new array. In particular, the device is capable of detecting the local peaks that correspond to heart rate. In general, the local peaks correspond to values of $\tau$ that correspond to delta $\Delta t$ having a frequency transform that gives the heart rate of the user from which the PPG data is obtained.

The device is capable of repeating the operations described three times with the mutual information bins being added to each prior bin. Once the mutual information output array is populated with the output of four separate and consecutive mutual information calculations, the device removes the first mutual information output array from the mutual information output array. More specifically, there exists an MI*($\tau$) that is calculated as shown in Expression 17.

$$MI^*(\tau) = MI_0(\tau) + MI_1(\tau) + MI_2(\tau) + MI_3(\tau) \tag{17}$$

Each $MI_i(\tau)$ is a completed value of mutual information at a specific time delay (lag). The device may then add the completed $MI_i(\tau)$ points to the other three values from three different windows. This process allows all four mutual information bins to be filled prior to allowing disabling of LEDs (e.g., PPG sensor). The mutual information is more sensitive to finger placement when the mutual information bins are not populated.

The device is capable of repeating the process with the exception that the mutual information output array becomes a sliding window of mutual information (e.g., previously referred to as MI*). For example, the device removes $MI_3$ from MI* and then $MI_i$ is shifted to $MI_{i+1}$, which frees $MI_0$. The device adds the newest calculation of MI to this empty buffer point and then calculates MI* again.

The device is capable of monitoring the relative change in MI (at the peak corresponding to heart rate). In one or more embodiments, if the mutual information falls too low, e.g., below a threshold mutual information level, the device determines that there is no more periodicity in the PPG data or an insufficient amount of periodicity in the PPG data. This implies that knowing X gives little information about X(t+$\tau$).

Figure 4:
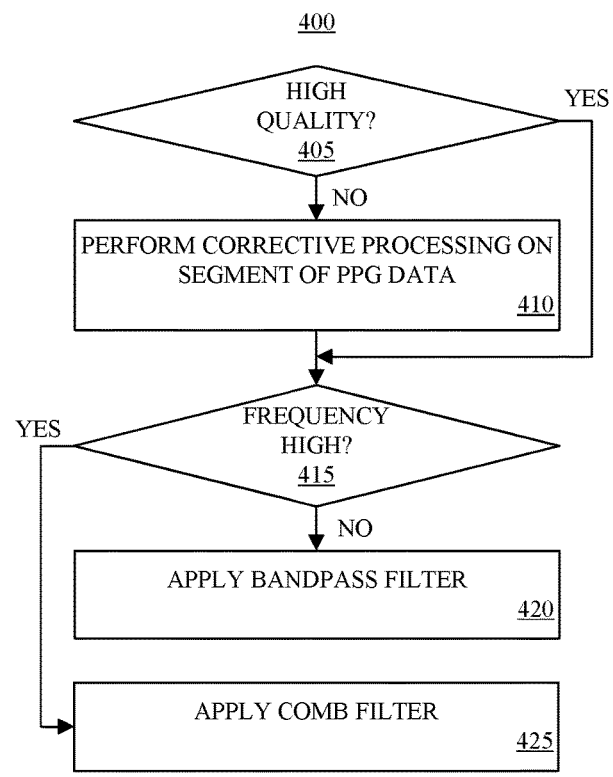
FIG. 4 illustrates an example method of filtering and/or correction for PPG data.

FIG. 4 illustrates an example method 400 correcting and filtering the PPG data. Method 400 may be performed by a device as described herein in connection with FIG. 1. In one or more embodiments, method 400 may be performed by the device to implement block 220 of FIG. 2.

In block 405, the device determines whether the quality of the segment is high. For example, the device is capable of classifying the segment of PPG data as described in connection with block 205 of FIG. 2 and block 315 of FIG. 3. In general, the device is capable of applying dynamic processing to the segment of PPG data based upon the estimated quality. In the example of FIG. 4, the device applies corrective processing to the segment of PPG data in response to determining that the quality is moderate (e.g., not high). Recalling from the prior discussion of FIGS. 2 and 3 that low-quality segments of PPG data are rejected in block 215, the device is dealing with PPG data that is classified as either high or moderate in block 405.

In response to determining that the quality of the segment of PPG data is high, method 400 continues to block 415. In that case, the device may skip corrective processing for the segment of PPG data. In response to determining that the quality of the segment is not high, e.g., is moderate, method 400 continues to block 410 where the device performs corrective processing for the segment of PPG data.

In block 410, the device is capable of performing corrective processing on the segment of PPG data. In one or more embodiments, the device de-noises the segment. In cases where the segment of PPG data is of moderate quality, the segment may be corrupted with different noise components (e.g., artifacts of motion) that are not inherent parts of basic PPG morphology.

In one or more embodiments, as part of block 410, the device is capable of applying a filter to remove high-frequency components of the PPG data that are not relevant to heart rate analysis. For example, the device is capable of filtering the segment of PPG data using a $5^{th}$ order IIR filter. The processing described may also work with derivative components of filtered PPG data with respect to time since the derivative peaks are more pronounced than the normal PPG data.

In one or more embodiments, the device is capable of performing a transform (e.g., a frequency transform) of the PPG data only in response to determining that the segment of PPG data includes sufficient noise to prevent unnecessary calculations. As an illustrative and nonlimiting example, the device is capable of using variance to determine whether the PPG data includes noise. The device is capable of calculating variance using a data set of accelerometer data. Accelerometer data is associated with increased motion artifacts. The device is capable of determining variance in the dataset (x), where x is an array of accelerometer values synchronized in time with the segment of PPG data.

The device is capable of parsing the array of accelerometer values into smaller segments. Each segment may include 50 values upon which the device determines variance. For each window, the device determines the variance and determines whether the calculated variance is greater than a threshold σ, where σ=0.3. In response to the variance exceeding the threshold, the device determines that segment of PPG data includes noise. If the variance does not exceed the threshold, the device determines that the segment of PPG data does not include noise and may omit performing any further corrective processing and omit performing any translation of the PPG data to the frequency domain using a transform. It should be appreciated that the specific values provided are for purposes of illustration and are not intended to be limiting.

In particular embodiments, where noise is detected using the accelerometer data, the device is capable of deconstructing the signal to filter out specific components. Since the processing described is performed in near real time, the device is capable of deconstructing segments of PPG data to occur within windows of a predetermined amount of time and/or number of samples. As an illustrative and nonlimiting example, the number of samples may be equal to 800.

In block 410, the device is capable of transforming the PPG data using a continuous complex wavelet transformation function. In particular embodiments, the device uses a Morlet wavelet to represent the PPG data. The device is capable of generating a first window of N-samples constructed with the point with detected noise (e.g., where σ>0.3) being centered in the window. Although edge-coefficient effects are mitigated with zero-padding of the wavelet function, the device is capable of centering the point of interest in the wavelet window. The Morlet wavelet is given by Expressions 18 and 19 below.

$$\psi_0(\eta) = \pi^{-\frac{1}{4}} e^{-i\omega\eta} e^{-\frac{\eta^2}{2}} \tag{18}$$

$$\psi\left(\frac{(n'-n)\delta t}{s}\right) = \left(\frac{\delta t}{s}\right)^{\frac{1}{2}} \psi_0\left(\frac{(n'-n)\delta t}{s}\right) \tag{19}$$

In the example of Expressions 18 and 19, s is called the dilation and is inversely related to the frequency being analyzed. In the example of FIG. 4, s is an array of values from lowest frequency $s_0=2*dt$ to higher multiples of $s_0$. The wavelet transform for each daughter wave (e.g., a scaled version of the Morlet mother) is computed on the discrete Fourier transformed ψ and p', $\hat{\psi}$ and $\widehat{p'}$, respectively.

$$\widehat{p'}_k = \frac{1}{N} \sum_{n=0}^{N-1} p'_n e^{-2\pi jkn/N} \tag{20}$$

$$W_n = \sum_{n=0}^{N-1} \widehat{p'}_k \hat{\psi}(s\omega_k) e^{j\omega_k n\delta t} \tag{21}$$

Referring to Expression 21, $W_n$ represents the wavelet coefficient array for a specific time index (n), where s is the independent variable inside the convolution. The s in Expression 21 is the scale of the wavelet and roughly is a frequency term. Each $W_n$ is a set of wavelet coefficients (corresponding to scale) at a particular time index. Expressions 20 and 21 evoke the convolution theorem by computing the inverse Fourier transform of the product shown in Expression 21. Expression 20 represents the Discrete Fourier Transform (DFT) of the signal window from the PPG data.

The signal p' window exists in a 2-d matrix with rows indicating time index for a specific scale (s) and columns representing real and imaginary components of the transform. The device is capable of converting the 2-d matrix into a scalar value by computing the complex modulus of the complex element.

The device is capable of calculating the magnitude of wavelet transform from a scale band corresponding to expected signal location. For this analysis, s=36 is appropriate size to capture a specific physiological signal. The device is capable of comparing this magnitude to the magnitude of the rest of the wavelet image. Since the suspected noise has already been centered in the window, a large magnitude is expected to be located at this center point.

The device is further capable of attenuating elements of the transform that are significantly larger than the mean scale band magnitude. In one or more embodiments, to avoid filtering artifacts during reverse transformation, the device is capable of attenuating the elements using a smooth blending function defined as a quadratic function with zero-crossings at each end of the noise window. As a result, the device applies minimum attenuation at the end points (smoothly blending with the side band spectrum) of the window and maximum attenuation at the center of the noisy portion.

Expression 22 illustrates filtering of the wavelet transform coefficients $W_n$ as a function of time index (n). As such, Expression 22 represents the attenuated signal, as the wavelet transform coefficients, that are later used for an inverse transform to recover the filtered time series.

$$W_n^* = \begin{cases} 4\frac{\left(n-\frac{l}{2}\right)^2}{l^2} W_n, & W_n > \|W_{n^*}\| \\ W_n, & W_n \le \|W_{n^*}\| \end{cases} \quad (22)$$

The device is further capable of reconstructing the PPG signal. In this example, an orthogonal transform is not presumed. As such, the device is capable of determining the inverse transformation using a delta function and sum the real components of $W_n^*$ with appropriate de-scaling coefficients.

Within this disclosure, a wavelet transform is used for purposes of illustration. The inventive arrangements are not intended to be limited by the examples provided. In other embodiments, for example, a different transform may be used. For example, another windowed frequency domain transform may be used in place of wavelets.

In block 415, the device determines whether the frequency of the signal is high based upon the periodicity of the signal as determined from the mutual information operations described in connection with block 205 of FIG. 2 and block 310 of FIG. 3. The device compares the frequency of the signal with a frequency threshold. In one or more embodiments, the frequency threshold may be set to a heart rate of 100 beats per minute (BPM) corresponding to a tachycardic signal. When the PPG signal is likely to be tachycardic (e.g., where heart rate exceeds 100 BPM), then an appropriately tuned Comb filter may be used for heart rate estimation. For PPG signals that are not tachycardic, such signals may be analyzed using another approach such as by applying a band pass filter.

Accordingly, in response to determining that the frequency of the PPG data is low (e.g., does not exceed the frequency threshold), method 400 continues to block 420. In block 420, the device applies a bandpass filter to the segment of PPG data. In response to determining that the frequency of the PPG data is high (e.g., exceeds the frequency threshold), method 400 continues to block 425. In block 425, the device applies a comb filter to the PPG data.

Figure 5:
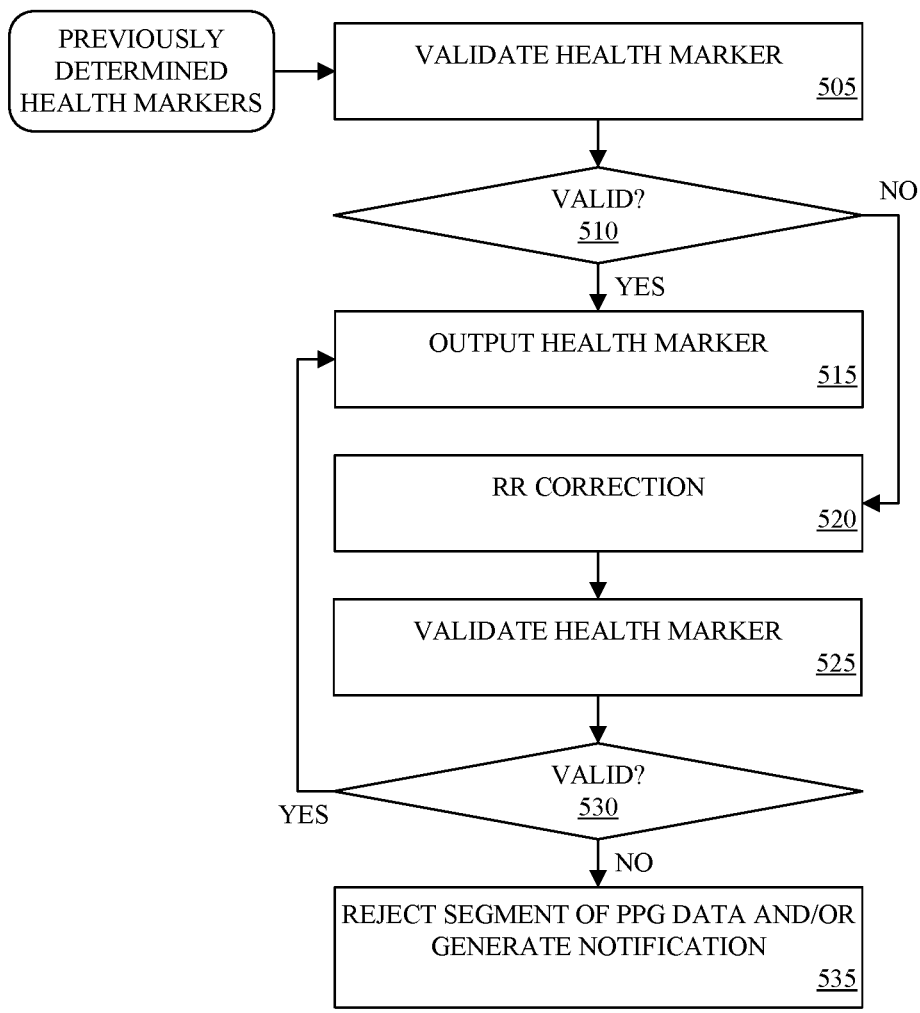
FIG. 5 illustrates an example method of validating a health marker.

FIG. 5 illustrates an example method 500 validating health marker(s). Method 500 may be performed by a device as described herein in connection with FIG. 1. In one or more embodiments, method 500 may be performed by the device to implement block 245 of FIG. 2. In particular embodiments, the device further performs post hoc correction of the PPG data.

In block 505, the device is capable of validating the health marker determined in block 240 of FIG. 2. In one or more embodiments, the device is capable of comparing the current health marker (e.g., the health marker determined in block 240) with recent historical measurements of the same type of health marker. As an illustrative and nonlimiting example, the device is capable of evaluating the most recent N estimates of heart rate for the user where N is an integer value. In this example, the time series of health markers have ten data items which are: 89 90 89 52 213 212 211 211 92 92 (in BPM). The example illustrates a likely error where the fluctuation in heart rate is first seen in the transition from the heart rate estimate of 89 to 52. Further, likely error is illustrated in the significant increase in estimated heart rate from 52 to 213, which continues until settling back to 92 in the $9^{th}$ value.

Accordingly, in one or more embodiments, the device is capable of determining whether health marker values in a time series of estimated heart rate values exceeds an upper limit or falls below a lower limit. The upper and lower limit may be known physiological limits for an individual of like or similar health as the user. The device is capable of discarding any health marker that is above the upper threshold or that is below the lower threshold. For example, in the example time series of heart rates, values such as 52, 213, 212, and 211 may be discarded.

In one or more embodiments, the device is capable of determining whether the amount of change between two successive health markers in a time series of health markers exceeds a threshold amount of change. If so, the device is capable of discarding the health marker(s) deemed to be inaccurate. Referring to the example data set of heart rates, the device may discard the heart rates of 52 and 213 as exhibiting too much of a change from the immediately prior heart rate.

In one or more embodiments, the device is capable of using inertial sensors to validate health markers for the user. The device, for example, is capable of determining an activity level of the user based upon inertial sensor data such as gyroscope sensor data, accelerometer sensor data, and/or position (location) data over time. The inertial data may be correlated with levels of activity and health markers such as heart rates, HRV, and the like for the user on a historical basis. Thus, the internal sensors may not only be used to indicate the likelihood of noise being within the PPG data as described herein in connection with FIG. 4 (e.g., block 410), but also may be used in establishing an expected range of health markers to which the health marker determined in block 240 may be compared for validation purposes.

For example, the device is capable of determining the level of activity for the user for a given point in time based upon inertial sensor data. The device is capable of determining a heart rate range for the user given the level of activity. The device is capable of comparing the heart rate determined in block 240 with the heart rate range. In response to determining that the estimated heart rate is within the heart rate range, the device is capable of determining that the heart rate of block 240 is valid. In response to determining that the heart rate of block 240 is either above or below the heart rate range, the device is capable of determining that the estimated heart rate is invalid.

In block 510, the device determines whether health marker is valid as described. In response to determining that the health marker is valid, method 500 continues to block 515. In block 515, the device outputs the health marker. For example, the device is capable of outputting the health marker to a display and/or storing the health marker in memory. In response to determining that the health marker is not valid, method 500 proceeds to block 520.

In block 520, the device is capable of performing RR correction on the segment of PPG data. For example, in cases where the health marker is determined to be invalid, the device is capable of performing a corrective action to obtain a valid health marker. As an illustrative and nonlimiting example, the device is capable of removing a peak in cases where the device determines that the health marker (e.g., heart rate) has increased from a prior measure of the health marker by approximately a factor of two. Referring to the prior example of estimated heart rates, the increase in heart rate estimates from approximately 92 to approximately 213 may have been the result of detecting an extraneous peak in the time series data. Removing a peak may bring the estimated heart rate back into acceptable tolerances.

In block 525, the device is capable of performing validation on the RR corrected segment of PPG data. The device is capable of performing block 525 substantially as described in connection with block 505. In block 530, the device determines whether the RR corrected segment of PPG data is valid. If so, method 500 loops back to block 520 to output the health marker using the RR corrected segment of PPG data. If not, method 500 continues to block 535.

In block 535, the device is capable of rejecting the segment of RR corrected PPG data and/or generating a notification. For example, the device is capable of deleting the RR corrected segment of PPG data. In rejecting the segment, for example, the device does not attempt to determine any health markers using the segment of RR corrected PPG data. Further, the device is capable of providing a notification indicating that the segment of PPG data is not suitable for use in determining health markers. In one or more embodiments, the notification may provide instructions to the user to adjust the device so as to obtain higher quality PPG data.

As discussed, in response to rejecting a segment of PPG data, the device is capable of generating a notification. In one or more embodiments, the device is capable of customizing the instructions that are provided based upon the particular aspect or dimension that was "failed" thereby causing rejection of the segment of PPG data. For example, the notification may indicate the particular test that was failed or particular aspect of the segment of PPG data deemed insufficient. The device further may provide instructions for adjusting a wearable device, for example, that are specific to the particular reason the segment of PPG data was determined to be of insufficient quality.

As an illustrative and non-limiting example, in response to determining that the relative pulsatile amplitude described in connection with block 225 indicates non-biological contact, the device is capable of generating a notification to the user. The notification may be a push notification indicating that no health markers are detected. Further, in response to detecting non-biological contact, the device is capable of powering off. The powering off may be triggered a predetermined amount of time after detecting the non-biological contact or in response to detecting non-biological contact for a predetermined or minimum amount of time. The powering off preserves battery life and also may prevent corruption of any further logging of data. The notification may also inform the user of the powering off. For example, the device may display a countdown to the powering off.

As another illustrative and non-limiting example, in response to determining that the wavelet processing described in connection with block 410 indicates a step response in the PPG data, the device is capable of generating a notification to the user. The notification may be a push notification. The type of noise detected in block 410 may be caused by loose contact between the device and the user. Accordingly, the notification may instruct the user to tighten the mechanism that couples the device to the user. In the case of a smart watch, for example, the notification may instruct the user to tighten the wrist band of the watch.

The terminology used herein is for the purpose of describing particular embodiments only and is not intended to be limiting. Notwithstanding, several definitions that apply throughout this document now will be presented.

As defined herein, the singular forms "a," "an," and "the" are intended to include the plural forms as well, unless the context clearly indicates otherwise.

As defined herein, the term "approximately" means nearly correct or exact, close in value or amount but not precise. For example, the term "approximately" may mean that the recited characteristic, parameter, or value is within a predetermined amount of the exact characteristic, parameter, or value.

As defined herein, the terms "at least one," "one or more," and "and/or," are open-ended expressions that are both conjunctive and disjunctive in operation unless explicitly stated otherwise. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, the term "automatically" means without user intervention.

As defined herein, the term "computer readable storage medium" means a storage medium that contains or stores program code for use by or in connection with an instruction execution system, apparatus, or device. As defined herein, a "computer readable storage medium" is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. The various forms of memory, as described herein, are examples of a computer readable storage media. A non-exhaustive list of more specific examples of a computer readable storage medium may include: a portable computer diskette, a hard disk, a random-access memory (RAM), a read-only memory (ROM), an erasable programmable read-only memory (EPROM or Flash memory), a static random-access memory (SRAM), a portable compact disc read-only memory (CD-ROM), a digital versatile disk (DVD), a memory stick, a floppy disk, or the like.

As defined herein, the term "if" means "when" or "upon" or "in response to" or "responsive to," depending upon the context. Thus, the phrase "if it is determined" or "if [a stated condition or event] is detected" may be construed to mean "upon determining" or "in response to determining" or "upon detecting [the stated condition or event]" or "in response to detecting [the stated condition or event]" or "responsive to detecting [the stated condition or event]" depending on the context.

As defined herein, the term "responsive to" and similar language as described above, e.g., "if," "when," or "upon," means responding or reacting readily to an action or event. The response or reaction is performed automatically. Thus, if a second action is performed "responsive to" a first action, there is a causal relationship between an occurrence of the first action and an occurrence of the second action. The term "responsive to" indicates the causal relationship.

As defined herein, the terms "one embodiment," "an embodiment," "one or more embodiments," "particular embodiments," or similar language mean that a particular feature, structure, or characteristic described in connection with the embodiment is included in at least one embodiment described within this disclosure. Thus, appearances of the phrases "in one embodiment," "in an embodiment," "in one or more embodiments," "in particular embodiments," and similar language throughout this disclosure may, but do not necessarily, all refer to the same embodiment. The terms "embodiment" and "arrangement" are used interchangeably within this disclosure.

As defined herein, the term "output" means storing in physical memory elements, e.g., devices, writing to display or other peripheral output device, sending or transmitting to another system, exporting, or the like.

As defined herein, the term "processor" means at least one hardware circuit. The hardware circuit may be configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "real time" means a level of processing responsiveness that a user or system senses as sufficiently immediate for a particular process or determination to be made, or that enables the processor to keep up with some external process.

As defined herein, the term "substantially" means that the recited characteristic, parameter, or value need not be achieved exactly, but that deviations or variations, including for example, tolerances, measurement error, measurement accuracy limitations, and other factors known to those of skill in the art, may occur in amounts that do not preclude the effect the characteristic was intended to provide.

As defined herein, the term "user" means a human being.

The terms first, second, etc. may be used herein to describe various elements. These elements should not be limited by these terms, as these terms are only used to distinguish one element from another unless stated otherwise or the context clearly indicates otherwise.

A computer program product may include a computer readable storage medium (or media) having computer readable program instructions thereon for causing a processor to carry out aspects of the present invention. Within this disclosure, the term "program code" is used interchangeably with the term "computer readable program instructions." Computer readable program instructions described herein may be downloaded to respective computing/processing devices from a computer readable storage medium or to an external computer or external storage device via a network, for example, the Internet, a Local Area Network (LAN), a Wide Area Network (WAN) and/or a wireless network. The network may include copper transmission cables, optical transmission fibers, wireless transmission, routers, firewalls, switches, gateway computers and/or edge devices including edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations for the inventive arrangements described herein may be assembler instructions, instruction-set-architecture (ISA) instructions, machine instructions, machine dependent instructions, microcode, firmware instructions, or either source code or object code written in any combination of one or more programming languages, including an object-oriented programming language and/or procedural programming languages. Computer readable program instructions may specify state-setting data. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some cases, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, may be implemented by computer readable program instructions, e.g., program code.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In this way, operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the operations specified in the flowchart and/or block diagram block or blocks.

The computer readable program instructions may also be loaded onto a computer, other programmable data processing apparatus, or other device to cause a series of operations to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the inventive arrangements. In this regard, each block in the flowchart or block diagrams may represent a module, segment, or portion of instructions, which comprises one or more executable instructions for implementing the specified operations. In some alternative implementations, the operations noted in the blocks may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

The corresponding structures, materials, acts, and equivalents of all means or step plus function elements that may be found in the claims below are intended to include any structure, material, or act for performing the function in combination with other claimed elements as specifically claimed.

The description of the embodiments provided herein is for purposes of illustration and is not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art to understand the embodiments disclosed herein. Modifications and variations may be apparent to those of ordinary skill in the art without departing from the scope and spirit of the described inventive arrangements. Accordingly, reference should be made to the following claims, rather than to the foregoing disclosure, as indicating the scope of such features and implementations.

What is claimed is:

1. A method, comprising:
   storing a plurality of segments of photoplethysmogram (PPG) data generated by a PPG sensor in a memory of a portable device;
   for each segment of the plurality of segments of PPG data, determining a quality estimate and deleting the segment in response to determining that the quality estimate does not exceed a quality threshold;
   for each remaining segment of the plurality of segments of PPG data, selecting a filter from a plurality of filters based on whether the segment is tachycardic and filtering the segment using the selected filter;
   determining, using a processor, a time series of health markers from the remaining segments of the plurality of segments of PPG data;
   validating, using the processor, the time series of health markers by discarding selected ones of the health markers in the time series of health markers that are not within a designated range; and
   outputting the validated health markers, wherein the segments of PPG data are processed in real time or near real time to determine and validate the time series of health markers.

2. The method of claim 1, wherein the PPG data is multichannel PPG data, wherein the determining the quality estimate comprises:
   determining covariance between PPG data corresponding to a first channel of the multichannel PPG data and PPG data corresponding to a second channel of the multichannel PPG data.

3. The method of claim 1, comprising:
   determining each remaining segment having a quality metric that is high and, for each remaining segment having a quality metric that is high, bypassing the selecting a filter and the filtering.

4. The method of claim 1, comprising:
   for each remaining segment of the plurality of segments of PPG data, discarding the segment in response to determining that the segment is not modulated by blood based on an AC component and a DC component of the segment of PPG data.

5. The method of claim 1, comprising:
   providing a notification that a segment of PPG data was rejected and not used to determine the health markers, wherein the notification indicates instructions for adjusting the portable device, the instructions correspond to a reason for rejecting the segment of PPG data, and the portable device includes the PPG sensor.

6. The method of claim 1, wherein the validating the time series of health markers comprises:
   determining whether health markers in the time series of health markers change by more than a predetermined amount.

7. The method of claim 1, wherein the validating the time series of health markers comprises:
   performing an RR correction of the segment of PPG data.

8. The method of claim 1, further comprising:
   de-noising the segment of the PPG data prior to the filtering.

9. The method of claim 8, further comprising:
   determining whether to perform the de-noising based upon inertial sensor data.

10. The method of claim 1, wherein the plurality of filters include a comb filter for use with segments that are tachycardic and a bandpass filter for use with segments that are not tachycardic.

11. The method of claim 1, wherein the health markers are heart rate.

12. The method of claim 1, wherein the health markers are heart rate variability.

13. The method of claim 1, wherein the health markers are stress.

14. A device, comprising:
   a photoplethysmogram (PPG) sensor configured to generate PPG data;
   a memory configured to store instructions;
   a processor coupled to the memory, wherein the processor, in response to executing the instructions, is configured to initiate operations including:
   storing a plurality of segments of the PPG data generated by the PPG sensor in the memory;
   for each segment of the plurality of segments of PPG data, determining a quality estimate and deleting the segment in response to determining that the quality estimate does not exceed a quality threshold;
   for each remaining segment of the plurality of segments of PPG data, selecting a filter from a plurality of filters based on whether the segment is tachycardic and filtering the segment using the selected filter;
   determining a time series of health markers from the remaining segments of the plurality of segments of PPG data;
   validating the time series of health markers by discarding selected ones of the health markers in the time series of health markers that are not within a designated range; and
   outputting the validated health markers, wherein the segments of PPG data are processed in real time or near real time to determine and validate the time series of health markers.

15. The device of claim 14, wherein the PPG data is multichannel PPG data, wherein the determining the quality estimate comprises:
determining covariance between PPG data corresponding to a first channel of the multichannel PPG data and PPG data corresponding to a second channel of the multichannel PPG data.

16. The device of claim 14, wherein the processor is configured to initiate operations comprising:
determining each remaining segment having a quality metric that is high and, for each remaining segment having a quality metric that is high, bypassing the selecting a filter and the filtering.

17. The device of claim 14, wherein the processor is configured to initiate operations comprising:
for each remaining segment of the plurality of segments of PPG data, discarding the segment in response to determining that the segment is not modulated by blood based on an AC component and a DC component of the segment of PPG data.

18. The device of claim 14, wherein the processor is configured to initiate operations comprising:
providing a notification that a segment of PPG data was rejected and not used to determine the health markers, wherein the notification indicates instructions for adjusting the portable device, the instructions correspond to a reason for rejecting the segment of PPG data, and the portable device includes the PPG sensor.

19. The device of claim 14, wherein the validating the time series of health markers comprises:
determining whether health markers in the time series of health markers change by more than a predetermined amount.

20. The device of claim 14, wherein the validating the time series of health markers comprises:
performing an RR correction of the segment of PPG data.

21. The device of claim 14, wherein the processor is configured to initiate executable operations further comprising:
de-noising the segment of the PPG data prior to the filtering.

22. The device of claim 21, wherein the processor is configured to initiate executable operations further comprising:
determining whether to perform the de-noising based upon inertial sensor data.

23. The device of claim 14, wherein the plurality of filters include a comb filter for use with segments that are tachycardic and a bandpass filter for use with segments that are not tachycardic.

24. The device of claim 14, wherein the health markers are heart rate.

25. The device of claim 14, wherein the health markers are heart rate variability.

26. The device of claim 14, wherein the health markers are stress.

27. A computer program product comprising a computer readable storage medium having program code stored thereon, the program code executable by a processor to perform operations comprising:
storing a plurality of segments of photoplethysmogram (PPG) data generated by a PPG sensor in a memory;
for each segment of the plurality of segments of PPG data, determining a quality estimate and deleting the segment in response to determining that the quality estimate does not exceed a quality threshold;
for each remaining segment of the plurality of segments of PPG data, selecting a filter from a plurality of filters based on whether the segment is tachycardic and filtering the segment using the selected filter;
determining a time series of health markers from the remaining segments of the plurality of segments of PPG data;
validating the time series of health markers by discarding selected ones of the health markers in the time series of health markers that are not within a designated range; and
outputting the validated health markers, wherein the segments of PPG data are processed in real time or near real time to determine and validate the time series of health markers.

28. The computer program product claim 27, wherein the PPG data is multichannel PPG data, wherein the determining the quality estimate comprises:
determining covariance between PPG data corresponding to a first channel of the multichannel PPG data and PPG data corresponding to a second channel of the multichannel PPG data.

29. The computer program product claim 27, wherein the program code is executable by the processor to perform operations comprising:
determining each remaining segment having a quality metric that is high and, for each remaining segment having a quality metric that is high, bypassing the selecting a filter and the filtering.

30. The computer program product claim 27, wherein the program code is executable by the processor to perform operations comprising:
for each remaining segment of the plurality of segments of PPG data, discarding the segment in response to determining that the segment is not modulated by blood based on an AC component and a DC component of the segment of PPG data.

31. The computer program product claim 27, wherein the program code is executable by the processor to perform operations comprising:
providing a notification that a segment of PPG data was rejected and not used to determine the health markers, wherein the notification indicates instructions for adjusting the portable device, the instructions correspond to a reason for rejecting the segment of PPG data, and the portable device includes the PPG sensor.

32. The computer program product claim 27, wherein the validating the time series of health markers comprises:
determining whether health markers in the time series of health markers change by more than a predetermined amount.

33. The computer program product claim 27, wherein the validating the time series of health markers comprises:
performing an RR correction of the segment of PPG data.

34. The computer program product claim 27, wherein the program code is executable by the processor to perform operations further comprising:
de-noising the segment of the PPG data prior to the filtering.

35. The computer program product claim 34, wherein the program code is executable by the processor to perform operations further comprising:
determining whether to perform the de-noising based upon inertial sensor data.

36. The computer program product claim 27, wherein the plurality of filters include a comb filter for use with segments that are tachycardic and a bandpass filter for use with segments that are not tachycardic.

37. The computer program product claim 27, wherein the health markers are heart rate.

38. The computer program product claim 27, wherein the health markers are heart rate variability.

39. The computer program product claim 27, wherein the health markers are stress.

* * * * *